United States Patent [19]

Mommessin et al.

[11] 4,248,599

[45] Feb. 3, 1981

[54] PROCESS FOR DETERMINING THE API GRAVITY OF OIL BY FID

[75] Inventors: Pierre R. Mommessin; John R. Castano; John G. Rankin, all of Houston; Mary L. Weiss, Spring, all of Tex.

[73] Assignee: Shell Oil Company, Houston, Tex.

[21] Appl. No.: 77,251

[22] Filed: Sep. 19, 1979

[51] Int. Cl.³ .................. G01N 31/12; G01N 21/72; G01N 9/00
[52] U.S. Cl. .................. 23/230 HC; 23/230 EP; 23/230 PC; 73/32 R; 422/54
[58] Field of Search ..... 23/230 HC, 230 EP, 230 PC; 422/54; 73/32 R

[56] References Cited

U.S. PATENT DOCUMENTS

| 3,753,654 | 8/1973 | Eggertsen | 23/230 PC |
| 3,953,171 | 4/1976 | Espitalie et al. | 23/230 EP |
| 4,153,415 | 5/1979 | Espitalie et al. | 23/230 EP |

Primary Examiner—Barry Richman

[57] ABSTRACT

The API gravity of an oil is determined by vaporizing its volatile and pyrolyzable components, measuring the ratio of the amount vaporized within a range of relatively high temperatures to the total amount vaporized and determining that the gravity of the oil being tested equals that of an oil which has a similar composition and which, when a substantially equal amount is tested under substantially the same conditions, yields a similar ratio of amounts vaporized at the same temperatures.

4 Claims, 2 Drawing Figures $$FID\ YIELD = \frac{(350-750\ °C)}{TOTAL\ HC\ YIELD} \times 100$$

PROCESS FOR DETERMINING THE API GRAVITY OF OIL BY FID

BACKGROUND OF THE INVENTION

This invention relates to determining the API gravity of an oil encountered within a subterranean reservoir. More particularly, the invention provides a relatively rapid method for determining the gravity of a relatively small amount of oil contained in or adsorbed on cores or bit cuttings or the like samples of a reservoir rock.

Determinations of oil gravities are known to be extremely valuable in the planning required during the development of an oil production prospect. The viscosity and volatility of a crude oil may vary quite widely with variations in API gravity, particularly with respect to gravities within about the 10°-20° API range. For example, in a typical heavy oil prospect, the change in viscosity which accompanies a change of from 11 to 12 degrees in API gravity is approximately 62 centipoises. But, the change in viscosity as the gravity changes from 18 to 19 degrees API is approximately only 3 centipoises. It is important to determine the oil gravity as precisely as possible and as early as possible in the predevelopment economic studies of an oil production prospect.

Previously used methods of determining the API gravity of an oil have included (a) direct measurements on oil samples recovered from production tests or samples obtained by formation fluid-sampling logging devices, or the like, (b) mud-gas chromatographic analyses, and (c) measurements of the refractive index (RI) of oil retorted from cores or samples of the reservoir formation. In the latter method, a calibration curve is prepared by retorting oils which have known gravities and similar chemical compositions and measuring the refractive indexes of the liquids condensed from the retorting. The gravity of the oil being tested is then determined by measuring the refractive index of its distillate and assuming that its gravity equals that of an oil of known gravity from which a distillate of similar refractive index is obtained.

The previously used methods have numerous disadvantages. Although the direct measurements are, of course, the most accurate, they are also the most expensive and time-consuming or require a relatively large sample. In a mud-gas analysis, due to variables which are apt to be encountered during drilling, the effects of various mud-gas components tend to be averaged out so that the measurements fail to provide usable API gravity data. Numerous ones of the lighter or more volatile components of a crude oil may be cracked or depolymerized during a retorting operation in which the vapors are condensed to a liquid. Because of this a property such as the refractive index of the distillate may vary from chemical composition and reactivity factors that are not related to the API gravity of the oil.

SUMMARY OF THE INVENTION

The present invention relates to a process for determining the API gravity of an oil. Volatile and pyrolyzable components of the oil are vaporized. A measurement is made of the ratio of the amount of hydrocarbon vapor produced at temperatures within a selected relatively high range to the total amount produced. The API gravity of an oil which has a similar composition and which, when a substantially equal amount is tested under substantially the same condition, yields a substantially equal ratio of amounts of hydrocarbons vaporized at the same temperatures is noted. The API gravity of the oil being tested is considered equal to that which was noted.

DESCRIPTION OF THE INVENTION

The present invention is at least in part premised on the following discoveries. A useful relationship exists between the above-described ratio of hydrocarbons vaporized and the API gravity of an oil. But, the magnitude of such a ratio varies with variations in the total weight of oil from which the hydrocarbons are volatilized. However, it is feasible to adjust the size of an oil-containing rock sample to provide a selected weight of oil for a comparative measurement.

The accuracy of an API gravity determination using such a ratio is generally as good as that obtained by refractive index determinations regarding the higher gravity oils. In addition, where the accuracy is most needed, it is significantly greater than that determined by refractive index for oils having relatively low gravities, such as those of from about 10°-20° API.

In the present process, the volatile and pyrolyzable hydrocarbon components of the oil should be vaporized and kept from condensing for a relatively short period during which measurements are made of the amounts of hydrocarbons which are vaporized at different temperatures. The use of a programmed temperature increase, from a temperature just high enough to vaporize most of the voltile components to a temperature high enough to pyrolyze substantially all of the pyrolyzable components, comprises a preferred procedure. A flame ionization detector comprises a particularly suitable means for measuring the amount of hydrocarbons vaporized at the particular temperatures. An electrically heated furnace is a particularly suitable means for heating the oil being tested and keeping the hydrocarbon vapors from condensing before their concentration is measured.

A particularly suitable temperature for initially vaporizing the volatile hydrocarbons is about 50° C. And, a particularly suitable range of realtively high temperatures for use in the above described ratio is from about 350° to 750° C. The minimum temperature between the oil sample and a flame ionization detector for measuring concentrations of hydrocarbon vapors is preferably kept at about 350° C. while the temperature of the oil being tested is increased from about 350° to 750° C. at a substantially uniform rate of, for example, about 25° C. per minute.

A particularly suitable apparatus and heating procedure for vaporizing the volatile and pyrolyzable hydrocarbons in an oil-containing sample and measuring the amounts of hydrocarbon vapor released at the specified temperatures, in accordance with the present invention, is described in U.S. Pat. No. 3,753,654 by Frank T. Eggertsen entitled "Method for Determining Organic Materials in Water".

Figure 1:
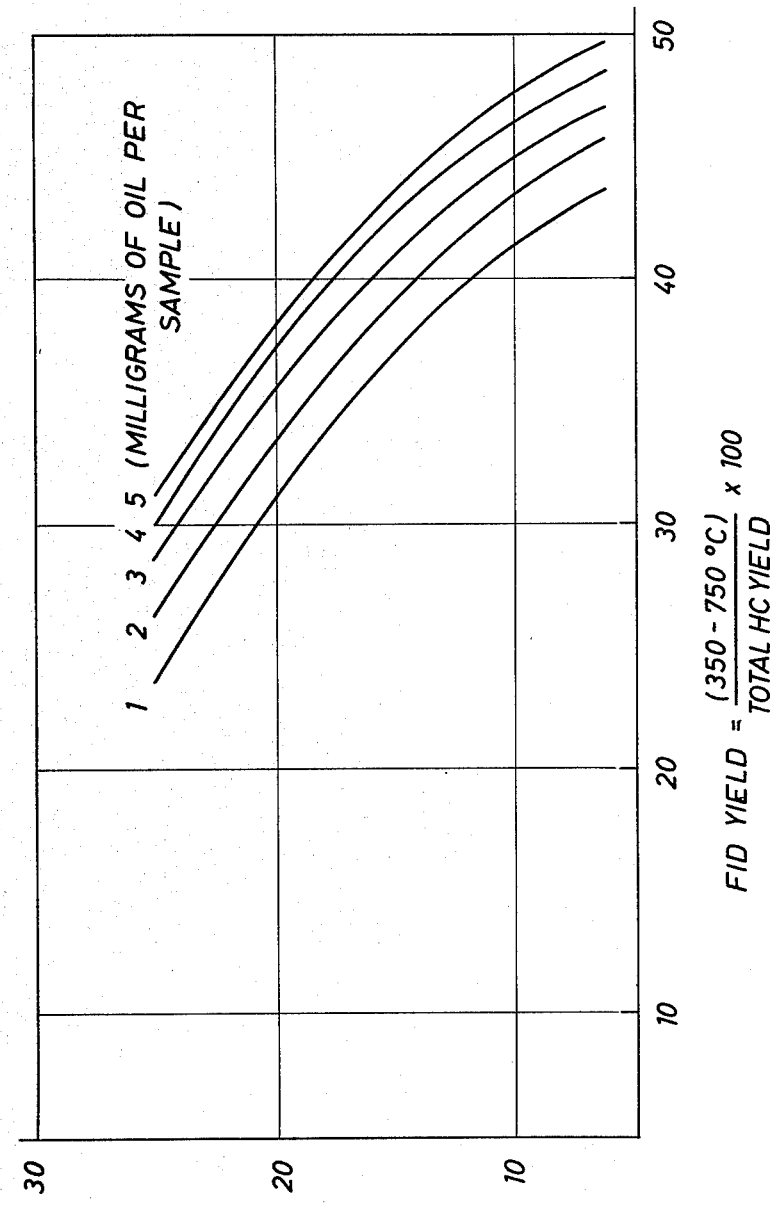
FIG. 1 is a graph showing the variation in API gravity with ratio of hydrocarbons vaporized and variations in sample size.

FIG. 1 shows a correlation between the API gravity and, respectively, the ratio of hydrocarbons vaporized at particular temperatures, and the weight of the oil in the sample being tested. The ratio of the amounts of hydrocarbons vaporized is expressed in terms of (a) the amount vaporized, as measured by a flame ionization detector, between the temperatures of 350° and 750° C. (b) the total amount of hydrocarbons vaporized, times 100. As indicated by the substantially parallel lines the amount of oil used is not particularly critical as long as the ratio obtained from a given amount of oil is compared with the ratio obtained from a similar amount of oil. In a preferred procedure the amount of oil used is preferably from about 2 to 5 milligrams.

The amount of oil which is present in a given rock sample can readily be determined by known procedures. A particularly suitable procedure is described in the article, "Show Descriptions from Core Sidewall and Ditch Samples" by R. E. Wyman and J. R. Castano, SPWLA 15th Annual Logging Symposium, June 2-5, 1974. In the preferred procedure, equal amounts of oil-stained rock sample and a volatile oil-solvent, such as chlorothene (1,1,1-trichloroethane) are mixed and agitated. The resultant solution is decanted and examined to determine color. Its fluorescence is then determined quantitatively using a fluorometer such as a Turner fluorometer. A log-log plot of the weight percent of hydrocarbon versus maximum fluorescence is then utilized to determine the amount of rock sample needed to provide a selected amount, such as a number of milligrams of oil. Such plots are prepared from fluorescence measurements on solutions of known concentration. In the above-described preferred type of oil vaporizing apparatus, the amount of rock sample can readily be varied from 20 to 200 milligrams in order to provide the selected amount of oil sample.

In the present process, in effect, the relationship between the ratio of vaporizable hydrocarbons and API gravity is determined by means of a calibration with oils expected to have similar chemical and physical characteristics to those encountered in the samples to be tested. In a preferred procedure, a series of calibration samples are prepared to duplicate as well as possible the chemical and physical state of the oils to be determined. It is particularly important that asphaltic oils be compared with asphaltic oils, paraffinic oils with paraffinic oils and the like. Direct determinations are made or obtained with respect to the calibration sample oils and those oils are mixed with finely divided rock materials, such as sand and water, at various appropriate saturations to provide oil-containing rock samples similar to those on which the oil-gravity determinations are to be made.

Figure 2:
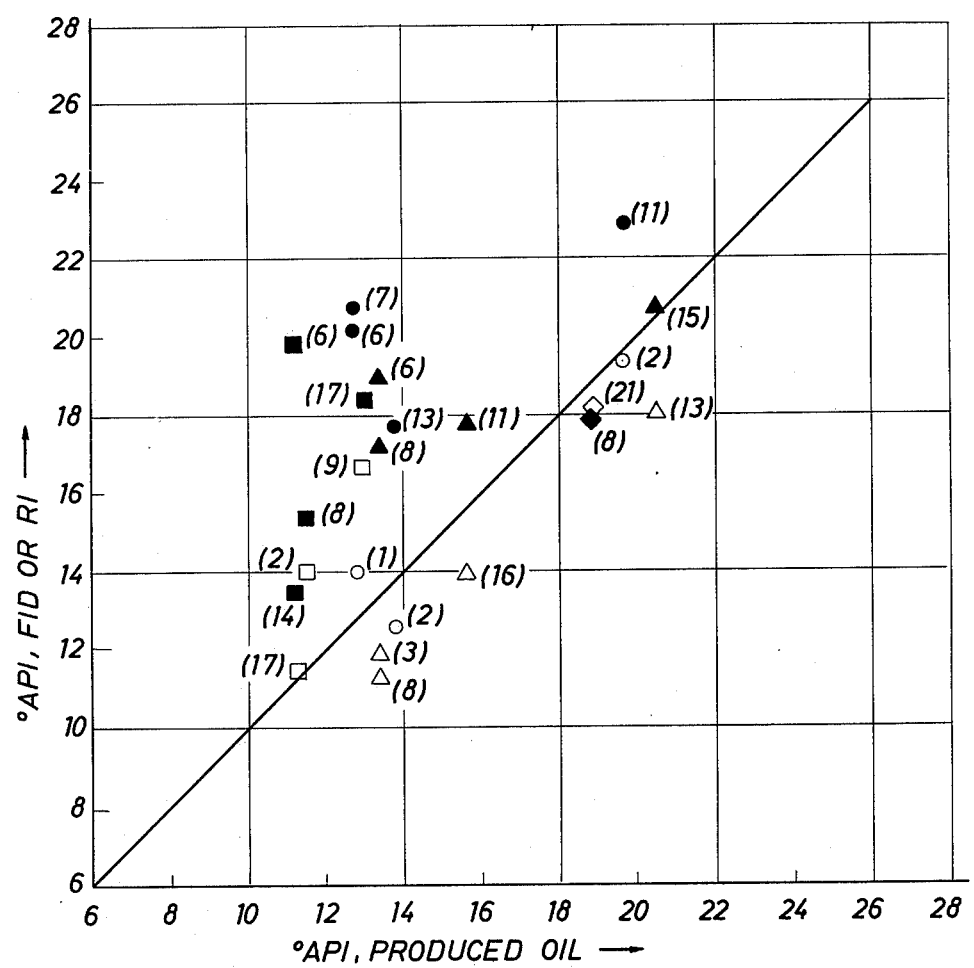
FIG. 2 shows a graphic comparison of RI ad FID measured gravities.

FIG. 2 shows a comparison of RI and FID measurements of API oil gravities on the oils from a series of four wells. The measured values were compared to the average gravities which were directly determined on the same oils and plotted (as a solid line) in accordance with a viscosity-weighted formula for the best relationship between the average oil gravity versus the produced oil gravity based on a typical crude oil viscosity-to-gravity relationship at 140° F. with the oils being gas-saturated to the extent existing within the reservoir. The individual measurements are plotted as circles triangles, etc., which are coded with respect to the well numbers. The numbers in parentheses by each of the plotted points indicate the number of samples on which measurements were averaged to obtain the plotted value. The refractive index (RI) measurements are indicated by the solid figures and the flame ionization detector (FID) measurements are indicated by the open figures. The FID measurements were made in accordance with the present process using the above-described preferred apparatus and temperatures.

FIG. 2 indicates that the RI measurements are generally high compared with the produced oil gravity. Where the produced oil gravity is less than 15° API, the RI measurements appear to be independent of the produced oil gravity, for the field involved. Where the produced oil gravity is greater than 16° API, both the RI and the FID methods compare rather well. Thus, the FID method appears to be generally suited for all oils and particularly well suited for low gravity oils.

Types of apparatus and measuring procedures which can suitably be used in practicing the present invention include the following:

A. Thermal analysis instruments and pyrolysers in which the evolution of volatile components can be followed as a function of temperature.

B. Distillation equipment, which avoids the above-mentioned problem of component-interaction during vapor condensation, and is suitable for the type of samples described above, is one in which a detailed true boiling point distillation curve, including a value for residue, is obtained. Such an instrument was described by Philyaw et al, 1971, Gas Chromatographic Analysis of Samples Containing both Volatile and Nonvolatile Organic Components, *Analytical Chem.*, v. 43, 787-789.

What is claimed is:

1. A process for determining the API gravity of an oil sample, comprising:

vaporizing volatile and pyrolyzable components of the oil sample;

measuring the ratio of the amount of the hydrocarbons vaporized at temperatures within a relatively high range of temperatures to the total amount vaporized;

noting the API gravity of an oil standard which has a similar chemical composition and which, when a similar amount is tested under substantially the same conditions, yields a substantially equal ratio of amounts of hydrocarbons vaporized; and, said step of noting being accomplished by reference to predetermined data relating said ratio to API gravity for a plurality of said oil standards, thereby determining the gravity of the oil being tested which approximately equals that which was so-noted.

2. The process of claim 1 in which the amounts of hydrocarbons vaporized are determined by means of a flame ionization detector.

3. The process of claim 1 or 2 in which the range of relatively high temperatures used in the measuring of said ratio is from about 350° C. to 750° C.

4. The process of claims 1 or 2 in which the oil sample being tested is contained within the pores or on the surfaces of finely divided rock materials weighing from about 20 to 200 milligrams and containing from about 2 to 5 milligrams of oil.

* * * * *